United States Patent [19]
Ohara

[11] 4,041,954
[45] Aug. 16, 1977

[54] SYSTEM FOR DETECTING INFORMATION IN AN ARTIFICIAL CARDIAC PACEMAKER

[75] Inventor: Yuichi Ohara, Tokyo, Japan

[73] Assignee: Kabushiki Kaisha Daini Seikosha, Japan

[21] Appl. No.: 575,129

[22] Filed: May 7, 1975

[30] Foreign Application Priority Data

May 7, 1974 Japan .............................. 49-50409
May 8, 1974 Japan .............................. 49-50831
May 14, 1974 Japan .............................. 49-53542

[51] Int. Cl.² .............................................. A61B 5/00
[52] U.S. Cl. ............................ 128/419 PT; 128/2.1 A
[58] Field of Search ........... 128/419 B, 419 C, 419 E, 128/419 P, 419 PG, 419 PS, 419 PT, 421, 422, 1.5, 2 P, 2 R, 2.1 A, 2.1 R

[56] References Cited

U.S. PATENT DOCUMENTS

| 3,032,029 | 5/1962 | Cunningham | 128/2.1 R |
| 3,253,588 | 5/1966 | Vuilleumier et al. | 128/2.1 A |
| 3,527,220 | 9/1970 | Summers | 128/1.5 |
| 3,625,199 | 12/1971 | Summers | 128/2 R |
| 3,662,758 | 5/1972 | Glover | 128/419 E |
| 3,672,352 | 6/1972 | Summers | 128/2.1 A |
| 3,826,265 | 7/1974 | Giori et al. | 128/419 PG |
| 3,841,336 | 10/1974 | Daynard | 128/419 PT |
| 3,853,117 | 12/1974 | Murr | 128/2 P |

*Primary Examiner*—William E. Kamm
*Attorney, Agent, or Firm*—Robert E. Burns; Emmanuel J. Lobato; Bruce L. Adams

[57] ABSTRACT

System for detecting information in an artificial cardiac pacemaker by using energy supplied from the outside of the pacemaker. An energy supplying device supplies energy to the pacemaker from the outside. An energy receiving device in the pacemaker receives the energy. An energy changing device changes the received energy into information energy, according to the information from an information generating device. An information transmitting device transmits the information energy to the outside of the pacemaker.

22 Claims, 27 Drawing Figures

SYSTEM FOR DETECTING INFORMATION IN AN ARTIFICIAL CARDIAC PACEMAKER

BACKGROUND OF THE INVENTION

1. Field of the Invention

The invention relates to a system for detecting information in an artificial cardiac pacemaker.

2. Description of the Prior Art

The cardiac pacemaker generally operates by battery energy. The operation of such cardiac pacemaker have a great influence on life or death of man; therefore, it is necessary to check the pacemaker operation, the power consumption of the battery in the pacemaker and the like, for always ensuring stable operation.

In order to check the inner state of the pacemaker, it is necessary to generate information signals corresponding to the inner state and to detect the information signals from a location outside the pacemaker.

Conventionally, a battery is used in the pacemaker, to supply the energy needed for generating the information signals and transmitting them to the outside of the pacemaker. It is desirable however, to minimize power consumption and to lengthen the life of the battery for the pacemaker implanted in the human body. Furthermore, as the pacemaker in the body is required to be small in size, the energy capacity of the battery is also small so that it is undesirable to use the battery energy in the pacemaker for transmitting the information signals because such shortens the life of the battery and the life of the pacemaker itself. It is also practically undesirable to provide another battery in the pacemaker for use in transmitting the information signals as this would increase the pacemaker size.

SUMMARY OF THE INVENTION

An object of the present invention is to provide a new and improved system for detecting information concerning the operation of an artificial cardiac pacemaker and which is extremely low in power consumption.

Another object of the present invention is to provide a new and improved system for detecting information about an artificial cardiac pacemaker without using the energy of the battery which powers the pacemaker.

Another object of the present invention is to provide a system for detecting information about an artificial cardiac pacemaker and which is small in size.

These and other objects have been attained by a system for detecting information about an artificial cardiac pacemaker which comprises energy supplying means for supplying energy to the artificial cardiac pacemaker from the outside, energy receiving means in the artificial cardiac pacemaker for receiving said energy, information generating means within the pacemaker for generating information signals representative of the battery voltage energy changing means for changing the energy through said energy signals receiving means into information energy according to said information, and information transmitting means for transmitting said information energy signals to the outside of said artificial cardiac pacemaker.

Other and further objects, features and advantages of the invention will appear more fully from the following description.

BRIEF DESCRIPTION OF THE DRAWINGS

FIGS. 5-1 to 5-4 are block diagrams showing embodiments of the energy supplying means for supplying several kinds of electromagnetic wave energy to the energy receiving means;

FIG. 6-1 is a block diagram, which includes a block diagram showing an embodiment of the energy supplying means for supplying sound wave energy and a circuit diagram showing an embodiment of the energy receiving means;

FIG. 6-2 is a block diagram of a modified form of the energy supplying means and the energy receiving means shown in FIG. 6-1;

DESCRIPTION OF THE PREFERRED EMBODIMENT

Figure 1:
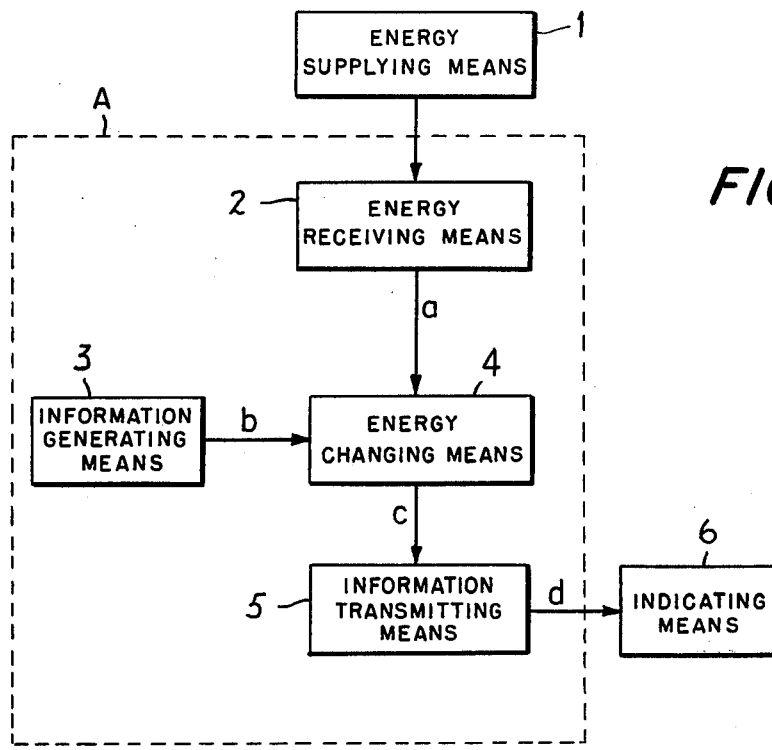
FIG. 1 is a block diagram of one form of system for detecting information about an artificial cardiac pacemaker according to the invention.

Referring now to FIG. 1, a system for detecting information about an aritificial cardiac pacemaker according to the invention comprises an energy supplying means 1, an energy receiving means 2, an information generating means 3, an energy changing means 4, an information transmitting means 5 and an indicating means 6.

The energy supplying means 1 generates energy, e.g., electro-magentic wave, sound wave, heat, mechanical vibration or the like, from a location outside of the artificial cardiac pacemaker "A", and supplies it into the pacemaker.

The energy receiving means 2 is provided in the pacemaker "A" and receives the energy from the energy supplying means 1. The receiving means 2 converts the received energy into predetermined energy as occasion demands and supplies the energy $a$ to the energy changing means 4.

The information generating means 3 generates an information signal $b$, e.g., an information signal representative of whether the battery in the pacemaker keeps up predetermined voltage, and supplies it to the energy changing means 4.

The energy changing means 4 changes the received energy $a$ derived from the energy receiving means 2 to an information energy signal $c$, according to the information signal $b$ carried from the information generating means 3. The information energy signal $c$ is carried to the information transmitting means 5. The transmitting means 5 converts the information energy signal $c$ into a proper energy form $d$ which can be transmitted to the outside of the pacemaker "A". The energy $d$ is transmitted to the indicating means 6.

The indicating means 6 so indicates the information in the pacemaker that one can understand it through one or more of the five senses.

Since the present invention is a system which gives energy for transmitting the information from the outside of the pacemaker, it is possible to reduce power consumption in the inner battery of the pacemaker. The battery in the pacemaker and the pacemaker, therefore, may be small in size.

Figure 2:
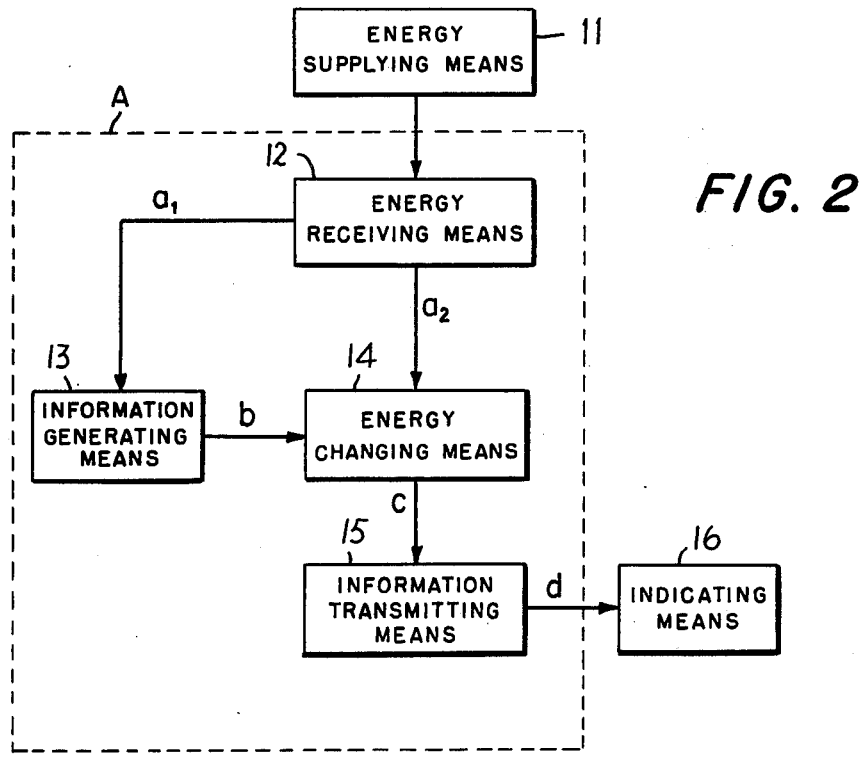
FIG. 2 is a block diagram of another form of the system according to the invention.

FIG. 2 shows another embodiment of the invention. In FIG. 2, and energy supplying means 11 generates energy outside of the pacemaker "A" and supplies it into the pacemaker.

An energy receiving means 12 is provided in the pacemaker "A" and receives the energy from the energy supplying means 11. The receiving means 12 converts the received energy into predetermined energy as occasion demands. A part $a_1$ of the energy through the receiving means 12 is carried to an information generating means 13, which generates information $b$. The information signal $b$ is carried to an energy changing means 14. The changing means 14 receives the other part $a_2$ of the energy through the receiving means 12, and changes it to an information energy signal $c$ according to the information $b$. The information energy signal $c$ is carried to an information transmitting means 15. The transmitting means 15 converts information energy signal $c$ into a suitable form of energy $d$ which can be transmitted to the outside of the pacemaker "A". The energy $d$ is transmitted to an indicating means 16. The indicating means 16 iso indicates the information in the pacemaker that one can understand it through the five senses.

In the embodiment, the system has a great effect, since energy from the outside of the pacemaker is used not only for transmitting the information but also for generating it. According to the system, it is possible to detect the information about the pacemaker without at all using the energy of the battery in the pacemaker.

For the energy supplying means 1 or 11, it is possible to adopt any device that generates electro-magnetic waves (electric waves, light, radiation and the like), sound waves (includes supersonic waves), heat, mechanicalvibration or the like. The energy receiving means 2 or 12 are selected according to the kind of energy given by the energy supplying means.

Figure 3:
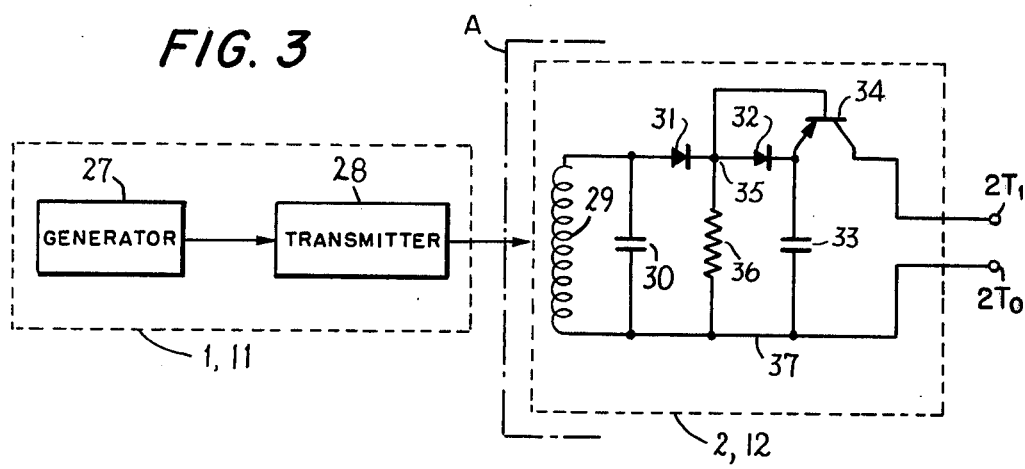
FIG. 3 is a block diagram, which includes a block diagram showing an embodiment of the energy supplying means for supplying electric wave energy or alternating magnetic field energy and a circuit diagram showing an embodiment of the energy receiving means.

In FIG. 3, there is shown an embodiment of the energy receiving means 2 or 12 with the energy supplying means 1 or 11 which generates electric wave energy or alternating magnetic field energy.

The energy supplying means 1 or 11 and the energy receiving means 2 or 12 shown in FIG. 3 will be explained in detail. The energy supplying means 1 or 11 comprises a well known high frequency generator 27 and a transmitter 28 for amplifying the output power of the generator 27 and modulating it as occasion demands and further for giving high frequency energy to the pacemaker "A".

The high frequency energy, e.g., electric waves or alternating magnetic field of electro-magnetic waves, may be the type of sine wave, pulse wave or saw tooth wave, and further may be either a non-modulated wave or modulated wave.

The energy receiving means 2 or 12 has a resonance circuit comprising a coil 29 for receiving the electric wave or alternating magnetic field transmitted from the energy supplying means 1 or 11 and a capacitor 30. The inductance of the coil 29 and the capacitance of the capacitor 30 are so determined that the circuit resonates with the electricwave or alternating magnetic field. The high frequency energy is induced in the coil 29, and accordingly, high frequency voltage is induced between both ends of the coil 29. The induced high frequency voltage is rectified in a half-wave rectifier comprised of diodes 31 and 32, and the rectified voltage is charged in a capacitor 33 for storing up energy. The higher potential end of the capacitor 33 is connected to the emitter of a transistor 34 of PNP type for performing a switching operation. The collector of the transistor 34 is connected to an output terminal $2T_1$ of the energy receiving means 2 or 12. The common connecting point 35 between the diodes 31 and 32 is connected to the base of the transistor 34 and an end of a resitor 36. The other end of the resistor 36 is connected to the line 37 that joins the lower potential end of the capacitor 33 with the other output terminal $2T_0$ of the energy receiving means 2 or 12.

While an electric wave or alternating magnetic field is being radiated from the transmitter 28, the potential of the higher side of the capacitor 33 is lower than the potential of the common connecting point 35 by the corresponding value owing to the threshold voltage of the diode 32. Consequently, in the transistor 34, the potential of the base becomes higher than the potential of the emitter; this makes the transistor 34 in the state of OFF, so that the output terminal $2T_0$ and $2T_1$ generate no output.

When the radiation of the electric wave or alternating magnetic field from the transmitter 28 is stopped, the potential of the base becomes lower than the potential of the emitter; this makes the transistor 34 in the state of ON as the potential of the common connecting point 35 turns equal low potential to that of the line 37 through the resistor 36. In response to the ON state of the transistor 34, the charge in the capacitor 33 appears on the output terminal. This in turn effects operation of the information generating means 13, the energy changing means 4 or 14 and the information transmitting means 5 or 15.

Figure 4:
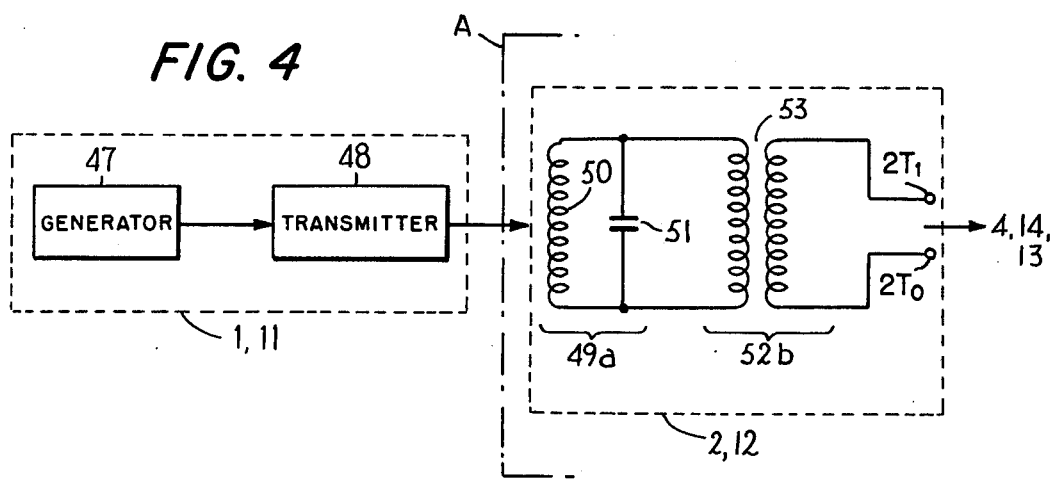
FIG. 4 is a block diagram of a modified form of the energy supplying means and the energy receiving means shown in FIG. 3.

In FIG. 4, there is shown another embodiment of the energy receiving means 2 or 12 with the energy supplying means 1 or 11 which generates electric wave or alternating magnetic field.

The energy supplying means 1 or 11 comprises well known generator 47 and a transmitter 48 similar to those in the embodiment of FIG. 3, and radiates high-frequency electro-magnetic wave energy. The electro-magnetic wave may be the type of sine wave, pulse wave or saw tooth wave, and further may be either a non-modulated wave or modulated wave.

The energy receiving means 2 or 12 has a pick-up part 49a and an output part 52b. The pick-up part 49a has a resonance circuit including a coil 50 and a capacitor 51. The inductance of the coil 50 and the capacitance of the capacitor 51 are so determined that the circuit resonates with the electro-magnetic wave. The output part 52b has a transformer 53, and gives the power induced in the pick-up part 49a to the energy changing means 4 or 14 and the information generating means 13 through the output terminals $2T_1$ and $2T_0$, without storing the power.

Figures 1, 5:
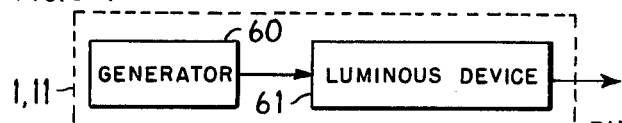
FIG. 5 is a block diagram showing an embodiment of the energy receiving means.
Figures 2, 5:
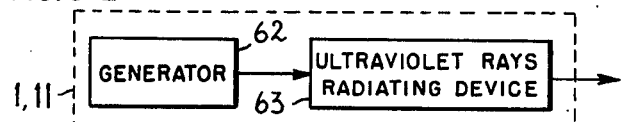
Figures 3, 5:
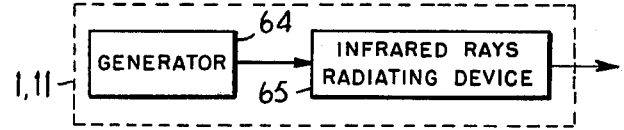
Figures 4, 5:
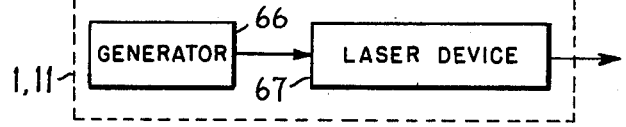
Figure 5:
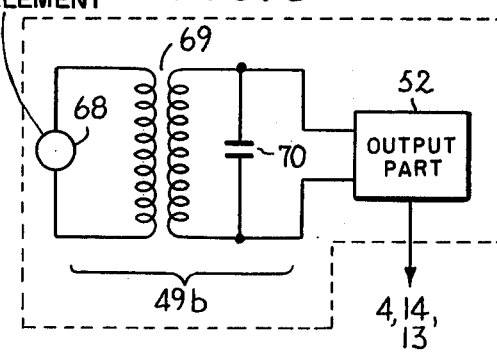

FIG. 5 illustrates an embodiment of the energy receiving means 2 or 12 which receives the light wave.

The energy supplying means 1 or 11 shown in FIG. 5-1 comprises a well known generator 60 and a luminous device 61, e.g., a sodium-vapor lamp, a mercury-arc lamp or a light emitting diode, which generates visible rays by using the AC electro-motive force given by the generator 60. The energy supplying means 1 or 11 shown in FIG. 5-2 comprises a generator 62 and an ultraviolet rays radiating device 63 which radiates ultraviolet rays by the output of the generator 62. The energy supplying means 1 or 11 shown in FIG. 5-3 comprises a generator 64 and an infrared rays radiating device 65. The energy supplying means 1 or 11 shown in FIG. 5-4 comprises a generator 66 and a laser device 67 which radiates laser rays having constant wavelength.

The light wave radiates from the energy supplying means 1 or 11 is modulated and is given to the energy receiving means 2 or 12 in the pacemaker "A".

The receiving means 2 or 12 has a pick-up part 49b for receiving the light wave and an output part 52 similar to that in the embodiment of FIG. 4. In the pick-up part 49b, a photoelectric element 68 receives light radiates from the energy supplying means 1 or 11 and accordingly generates electromotive force. The electromotive force is resonated by a transformer 69 and a capacitor 70, and is carried to the output part 52. The output of the output part 52 is given to the energy changing means 4 or 14 and the information generating means 13.

Figures 1, 6:
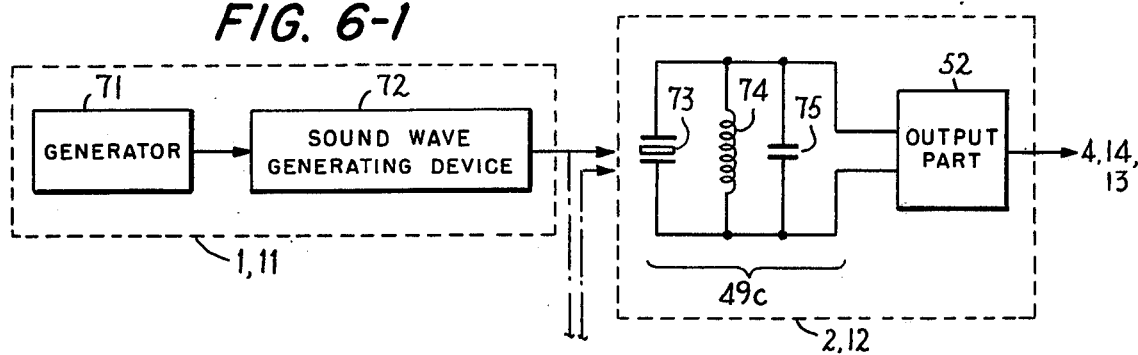
Figures 2, 6:
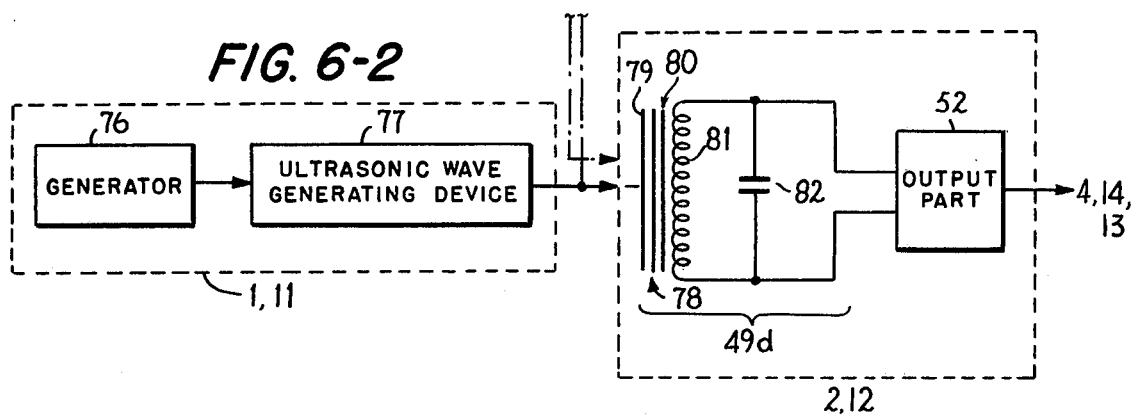

FIg. 6 illustrates two embodiments of the energy supplying means 1 or 11 for generating sound wave and the energy receiving means 2 or 12 for receiving the sound wave.

The energy supplying means 1 or 11 shown in FIG. 6-1 comprises a generator 71 and a well-known sound wave generating means 72 which generates particularly audio-sound waves.

The energy receiving means 2 or 12 has a pick-up part 49c for receiving the sound wave and an output part 52 similar to that in the embodiment of FIG. 4. In the pick-up part 49c, a piezoelectric element 73, e.g., quartz, Rochelle salt and barium titanate, generates an electromotive force by receiving the sound wave from the suppling means 1 or 11. The electromotive force is resonated by a coil 74 and a capacitor 75, and is carried to the output part 52. The output of the output part 52 is given to the energy changing means 4 or 14 and the information generating means 13.

FIG. 6-1 shows another embodiment using sound wave. In FIG. 6-2, the energy supplying means 1 or 11 generates ultrasonic wave through an ultrasonic wave generating device 77 by using the output of a generator 64. The energy receiving means 2 or 12 has a pick-up part 49d and an output part 52 similar to that in the embodiment of FIG. 4. In the pick-up part 49d, a dynamo 78 has a vibrating film 79, an iron core 80 and a coil 81. The vibrating film 79 is vibrated by the sound wave including ultrasonic wave from the supplying means 1 or 11, so that electromotive force is causd on the coil 81. The electromotive force is resonated by a capacitor 82, and is carried to the output part 52.

It is possible to exchange each energy receiving means 2 or 12 shown in FIG. 6-1 and 6-2 for each other. For example, it is possible to receive the sound wave from the sound wave generating device 7.' by the pick-up part 49d.

Figure 7:
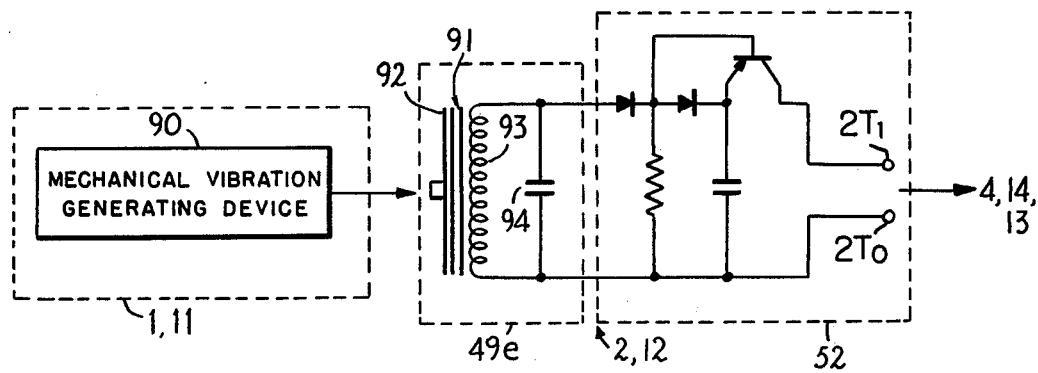
FIG. 7 is a block diagram, which includes a block diagram showing an embodiment of the energy supplying means for supplying mechanical energy and a circuit diagram showing an embodiment of the energy receiving means.

In FIG. 7, there is shown an embodiment of the energy supplying means 1 or 11 which generates mechanical energy and the energy receiving means 2 or 12.

The supplying means 1 or 11 has a well known mechanical vibration generating device 90 which generates mechanical vibration. The receiving means 2 or 12 has a pick-up part 49e receiving the mechanical vibration and an output part 52, which sends an output after storing the received energy, similar to that in the embodiment of FIG. 3.

The pick-up part 49e has a dynamo 91 which comprises a movable piece of iron 92 and a coil 93, and a capacitor 94. The inductance of the coil 93 and the capacitance of the capacitor 94 are so determined that the circuit resonates with the high-frequency energy from the dynamo 91. The output of the output part 52 is carried to the energy changing means 4 or 14 and the information generating means 13 through output terminals $2T_1$ and $2T_0$, in a similar manner to that in the embodiment of FIG. 3.

Figure 8:
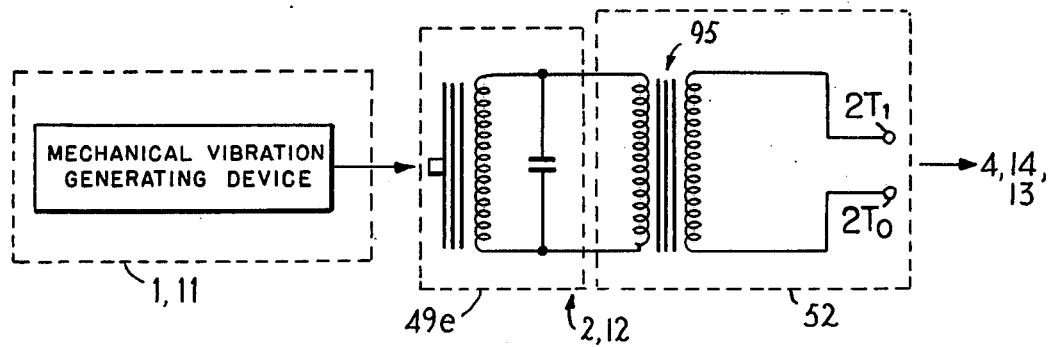
FIG. 8 and 9 are block diagrams of modified forms of the energy supplying means and the energy receiving means shown in FIG. 7.

FIG. 8 shows an embodiment of the energy supplying means 1 or 11 similar to that in FIG. 7 which generates mechanical vibration, and the energy receiving means 2 or 12. The energy receiving means 2 or 12 has a pick-up part 49e similar to that in FIG. 7 and an output part 52 including a transformer 95. The electric power induced in the pick-up part 49e is directly carried to the energy changing means 4 or 14 and the information generating means 13 through the transformer 95 and output terminals $2T_1$ and $2T_O$, without being stored.

Figure 9:
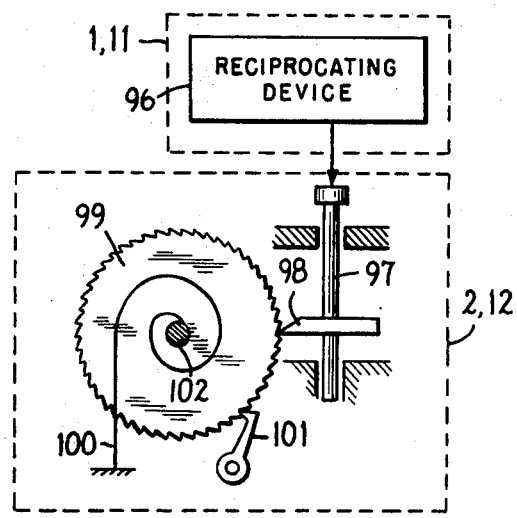

Another embodiment of the energy supplying means 1 or 11 which generates mechanical energy and the energy receiving means 2 or 12 is shown in FIG. 9.

The supplying means 1 or 11 has a reciprocating device 96 for giving the receiving means 2 or 12 reciprocating energy. The receiving means 2 or 12 comprises a sliding rod 97 having a feed pawl 98, a ratchet wheel 99 having a spiral spring 100 for storing the received energy and a pawl 101 for preventing the reverse rotation. The mechanical energy supplied from the reciprocating device 96 makes the ratchet wheel 99 rotate so that the rotational energy is stored in the spring 100. The energy stored in the spring 100 may be used through the shaft 102 of the ratchet wheel 99.

Figure 10:
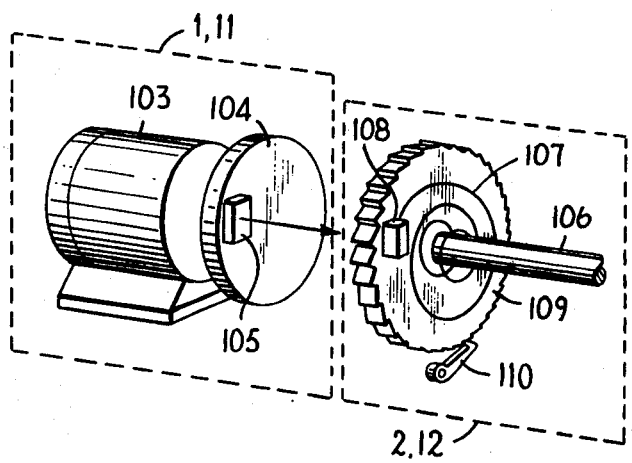
FIG. 10 is a perspective view showing another embodiment of the energy supplying means for supplying mechanical energy and the energy receiving means.

Another embodiment of the energy supplying means 1 or 11 which generates mechanical energy and the energy receiving means 2 or 12 is shown in FIG. 10.

The supplying means comprises a rotating device 103, which has a rotating disc 104 with a magnet 105.

The receiving means has a shaft 106, a spiral spring 107 provided around the shaft 106, a ferromagnetic material 108, e.g., a permanent magnet, provided on a ratchet wheel 109 and being fixed to one end of the spring 107, and a pawl 110 for preventing the reverse rotation. When the rotating disc 104 rotates together with the magnet 105, the ratchet wheel 109 and the ferromagnetic material 108 is made to rotate by the magentic flux from the magent 104. Consequently, energy is stored in the spring 107 and the energy may be used through the shaft 106 of the ratchet wheel 109.

Figure 11:
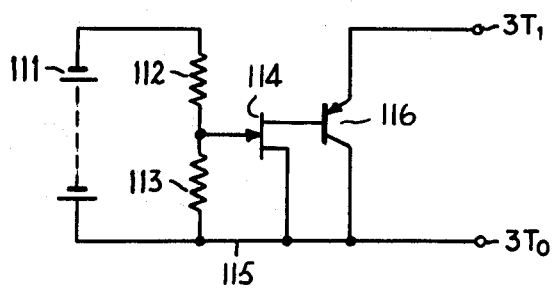
FIG. 11 is a circuit diagram showing an embodiment of the information generating means.

An embodiment of the information generating means 3 or 13 is illustrated in FIG. 11. The circuit generates an information signal as to whether the battery output in the pacemaker is above a predetermined e.m.f. In FIG. 11, batteries 111 are in the pacemaker "A" and are connected to bleeder high resistances 112 and 113 which are connected in series. The node between the bleeder resistances 112 and 113 is connected to the gate terminal of an N-channel Junction FET 114. The source terminal of the FET 114 is connected to the higher potential line 115 which joins the positive terminal of the batteries 111 with an output terminal $3T_0$ of the information generating means 3 or 13. The drain terminal is connected to the base of a transistor 116 of PNP type which operates as a switch. The collector of the transistor 116 is connected to the higher potential line 115, and the emitter is connected to the other output terminal $3T_1$ of the information generating means 3 or 13. The output terminals $3T_1$ and $3T_0$ send the information signal to the energy changing means 4 or 14.

While the batteries 111 produce the desired e.m.f., the gate voltage in the FET 114 is lower than the pinch-off voltage. The FET 114 is, therefore, in the state of OFF, and the impedance between the drain and the source is high. Consequently, the transistor 116 carries no current and is in the state of OFF, so that no output appears on the output terminals $3T_0$ and $3T_1$.

When the e.m.f. of the batteries 111 is gradually decreased in accordance with the consumption of the batteries and the gate voltage of the FET 114 becomes higher than the pinch-off voltage, the impedance between the source and the drain is decreased, so that the FET 114 becomes in the state of ON. According to the ON state of the FET 114, the base current of the transistor 116 begins to flow, so that the transistor 116 becomes in the state of ON. The output of the transistor is supplied to the energy changing means 4 or 14 through the output terminals $3T_0$ and $3T_1$ as the information signal.

An embodiment in the case of using a Junction Gate FET is illustrated in FIG. 6. It is also possible, however, to use an MOS FET. In this case, it is necessary to reverse the connection of the batteries.

Figure 12:
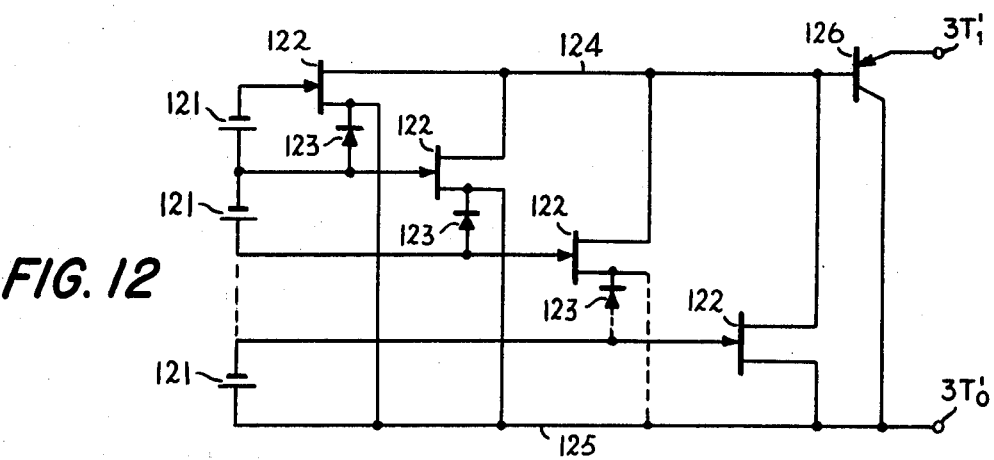
FIG. 12 is a circuit diagram showing another embodiment of the information generating means.

Another embodiment of the information generating means 3 or 13 is illustrated in FIG. 12.

This is what detects a decrease of the e.m.f. and generates an information signal indicative thereof, when a single battery's e.m.f. of the bank of batteries 121 in series which are provided in the pacemaker is decreased. The batteries 121 are connected in series with each other. As shown in FIG. 12, each gate terminal of N-channel Junction FET's 122 is respectively connected to each negative terminal of the batteries. Each drain terminal of the FET's is connected to a common line 124. Each source terminal is connected to a line 125 which carries positive voltage of the series batteries to the output terminal. Moreover, the cathode of each diode 123 is connected to the source of each FET 122 and the anode is connected to the positive terminal of the corresponding battery, as shown in FIG. 12.

The line 124 is connected to the base of a transistor 126 which operates as a switch. The line 125 is connected to the collector of the transistor 126 and an output terminal $3T_0'$ of the information generating means 3 or 13. The emitter of the transistor 126 is connected to the other output terminal $3T_1'$ of the means 3 or 13.

While every battery 121 holds a higher e.m.f. than the predetermined e.m.f., the gate voltage of each FET 122 is lower than the pinch-off voltage, so that each FET 122 is in the OFF state and the transistor 126 is thereby in the OFF state.

When one the battery's e.m.f. of batteries 121 becomes lower than the predetermined value, the gate potential of the FET 122 corresponding to the battery 121 rises as against the source potential and the gate voltage becomes higher than the pinch-off voltage. Consequently, the FET 122 turns to the ON state and the transistor 126 turns state On state too. The output in the ON state of the transistor 126 is supplied to the energy changing means 4 or 14 through the output terminals $3T_1'$ and $3T_0'$, as the information signal of the information generating means 3 or 13.

In the embodiment shown in FIG. 11, a portion of the energy of the batteries is wastefully dissipated through the bleeder resistances 112 and 113. By using high bleeder resistances having several tens MΩ, however, the wastefull dissipation is practically negligible for it is very little by comparison with the current dissipated in the pacemaker.

The circuit of the embodiment shown in FIG. 12 has only extremely little leakage current, i.e., gate current, so that the circuit has an advantage that the battery energy is hardly at all wastefully dissipated, according to the feature of FET input impedance of which is very high.

Figure 13:
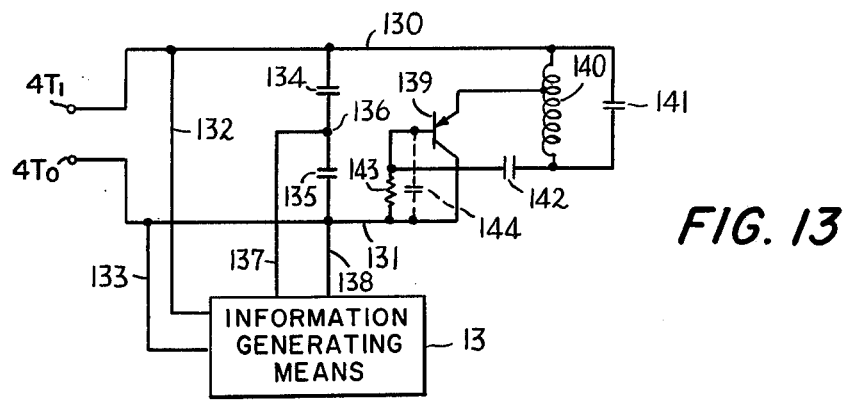
FIG. 13 is a circuit diagram showing an embodiment of the energy changing means.

FIG. 13 shows an embodiment of the energy changing means 14 shown in FIG. 2, that is made to operate by the received energy of the energy receiving means 12, and an embodiment of the information transmitting means 15.

Each of these means will be explained in detail. Each input terminal $4T_1$, $4T_0$, for the received energy is respectively connected to the output terminal $2T_1$, $2T_0$ of the energy receiving means 12.

The information generating means 13 is made to operate by a part of the received energy supplied through the line 132 that branches from the higher potential line 130 connected to the input terminal $4T_1$, and through the line 133 that branches from the lower potential line 131 connected to the input terminal $4T_0$. Between the higher potential line 130 and the lower one 131, two capacitors 134 and 135 are connected in series. Such capacitors 134 and 135 have a function similar to that of the energy changing means 14. The common connecting point 136 between the capacitors 134 and 135 is connected to an output terminal of the information generating means 13 through a line 137. The other output terminal of the information generating means 13 is connected to the lower potential line 131 through a line 138.

The information transmitting means 15 is composed of a known Hartly oscillator using a transistor. The oscillator includes a transistor 139, the collector of which is connected to the lower potential line 131, known as a grounded-collector transistor, an oscillating coil 140 an end of which is connected to the higher potential line 130 and the other end is connected to the base of the transistor 139 through a capacitor 142 and further which has intermediately a tap connected in parallel to the emitter, a capacitor 141 connected to the oscillating coil 140, and a resistor 143 an end of which is connected to the base and the other end is connected to the lower potential line 131. The numeral 144 indicated by a dotted line shows the stray capacity between the base and the collector. If needed, a capacitor having desired capacity may be connected there.

Figure 14:
FIG. 14 shows waveforms useful in explaining the operation of the information transmitting means.

The afore-mentioned oscillator composing the information transmitting means 15 generates high-frequency oscillation depending upon the constant of the oscillating coil 140 and the constant of the capacitor 141. When the stray capacity 144 is charged through the emitter, the oscillation is stopped according to a rise of the base potential in the transistor 139. Subsequently, when the stray capacitor 144 is discharged through the resistor 143 and capacitor 142, the oscillation is started again according to a drop of the base potential. Consequently, theoretically, it should intermittently repeat such high-frequency oscillation as shown in FIG. 14-A. The oscillator is made to operate by the received energy of the energy receiving means 12, e.g., the charge in the capacitor 33 shown in FIG. 3. The energy is supplied to the oscillator, after it is once charged in the capacitors 134 and 135. In fact, the output of the oscillator has waveform which on the decrease in the oscillating area shown in FIG. 14-B, according to the existence of the capacitor 144 and resistor 143.

In order to make the repeated output of the oscillator an audio frequency output, the capacitances of the capacitors 134, 135 and 142 and the resistance of the resistor 143 are set to suitable values. If the indicating means 16 is composed of a well-known receiving device for receiving the high frequency output of the oscillator, i.e., the information energy output of the information transmitting means 15, the detecting output results in an audio low-frequency signal corresponding to the repeated high-frequency output.

When an information signal supplied from the information generating means 13 is such one as short-circuits the capacitor 135 through the lines 137 and 138, the oscillator generates an output the waveform of which is different from one shown in FIG. 14-B in the oscillation starting area and the stopping area, corresponding to the content of the information signal. Consequently, the tone of the audio low-frequency sound received by the indicating means 16 is changed. By the change of the tone, one is able to understand the information.

As described hereinbefore, the received energy of the energy receiving means 12 is modulated by the energy changing means 14 which is composed of the capacitor 135, which is short-circuited corresponding to the information output of the information generating means 13, and the capacitor 134 connected in series. The output of the energy changing means 14 is radiated out of the pacemaker "A" through the information transmitting means 15, which is composed of the oscillator involving the transistor 139, as an information energy.

In the above-mentioned embodiment, the audio frequency pulse wave, the carrier wave of which is high frequency, is used as an information energy signal. It is also possible, however, to use what modulates the amplitude of a high-frequency continuous wave or the frequency of it, as an information energy signal.

The embodiment of the energy changing means and information transmitting means shown in FIG. 13 is one that is used for the system shown in FIG. 2. It is possible, however, to use the embodiment shown in FIG. 13 for the system shown in FIG. 1, if the input lines 132 and 133 of the information generating means 13 are cancelled. In this case, the information generating means 3 sends the information signal through the lines 137 and 138, by using a little energy of the battery in the pacemaker.

Figure 15:
FIG. 15 is a circuit diagram showing an embodiment of the energy changing means and the information transmitting means with a block diagram of the information generating means.
Figure 15:
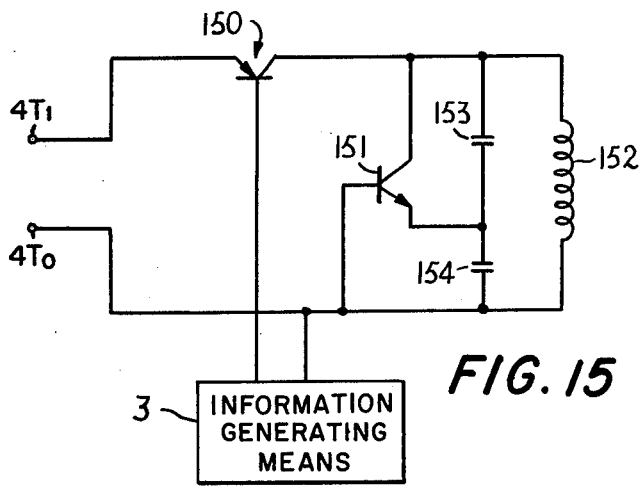

Another embodiment of the energy changing means 4 and the information transmitting means 5 is shown in FIG. 15. The energy changing means 4 has a transistor 150 which operates as a switch in response to the output of the information generating means 3. The information transmitting means 5 has a Colpitts oscillator comprising a transistor 151, an oscillating coil 152 and capacitors 153 and 154.

The transistor 150 turns into its ON or OFF state in response to the information signal of the information generating means 3. According to the ON state of the transistor, there appears high-frequency oscillation, the frequency of which is determined by the inductance of the coil 152 and the capacitance of the capacitors 153 and 154. The high frequency energy is radiated to the outside of the pacemaker "A", as electric wave energy.

In the embodiment, it is difficult to check whether the energy receiving means 2, the energy changing means 4 and the information transmitting means 5 operate properly, for no information energy is carried out of the transmitting means 5 while there appears no information from the information generating means 3.

Figure 16:
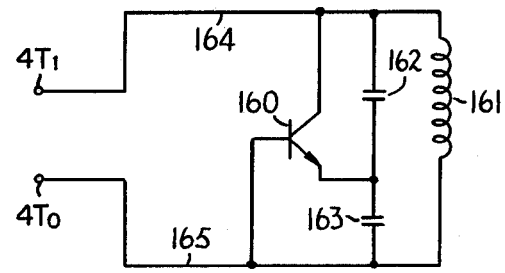
FIG. 16 is a circuit diagram showing an additional circuit for the information transmitting means.

It is possible to solve the problem by appending the oscillating circuit shown in FIG. 16 to the circuit shown in FIG. 15. The circuit shown in FIG. 16 is a Colpitts oscillator comprising a transistor 160, an oscillating coil 161 and capacitors 162 and 163. The circuit receives the stored energy, e.g., the energy stored in the capacitor 33 of the energy receiving means 2 shown in FIG. 3 through the lines 164 and 165, and continues to oscillate independently of the information generating of the means 3. The frequency of the oscillator is set approximately to the frequency of the oscillator shown in FIG. 15, and is so set that the difference of these frequencies is in the audio range. While no information is carried out of the information generating means 3, the indicating means 6 receives only the energy generated by the oscillator shown in FIG. 16. Consequenly, it is possible to confirm whether the energy receiving means 2 operates properly, by setting the indicating means 6 to indicate by the energy. When there appears the information from the information generating means 3, beat tone corresponding to the difference of the frequencies of the oscillator shown in FIG. 15 and FIG. 16 is generated by the indicating means 6, so that it is possible to understand the information, in case of the means 6 indicating the information by using audio sound.

Figure 17:
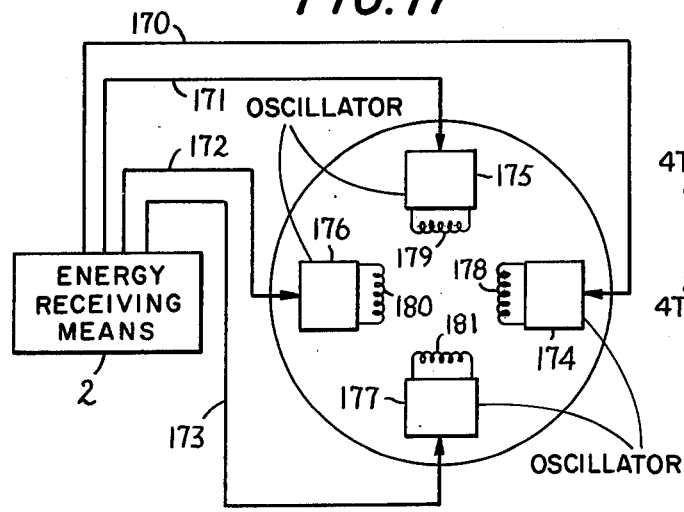
FIG. 17 is a schematic block diagram showing an embodiment of the energy receiving means, the energy changing means and the information transmitting means, for checking several kinds of information about the pacemaker.

FIG. 17 shows an embodiment of the energy changing means 4 and the information transmitting means 5, in case of the information generating means 3 generating several kinds of the information. In FIG. 17, lines 170, 171, 172 and 173 supply the energy from the energy receiving means 2 to several osciallating devices 174, 175, 176 and 177. The oscillating devices 174, 175, 176 and 177 have coils 178, 179, 180 and 181 respectively, which act as not only oscillating coils but also output coils. Each oscillating device 174 to 177 oscillates respectively when each device receives correspondingly the information signal from the information generating means 3 or 13, and puts out a signal, as the information energy signal, through each output coil 178 to 181. The indicating means 6 or 16 has same number of receiving coils and is set at the same form in position as compared with oscillating devices 174 to 177 and receives each signal, and an indicator corresponding to each signal indicates its operation so that one can understand which of the information signals is put out.

Figure 18:
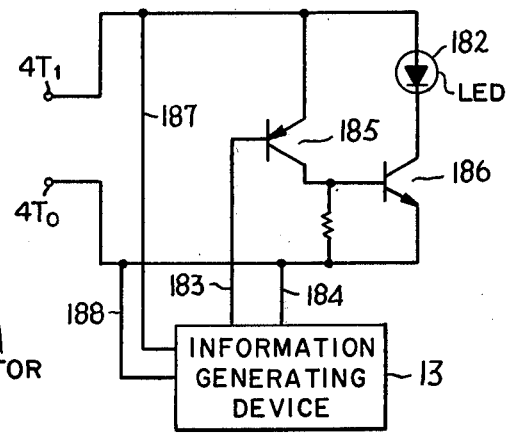
FIG. 18 is a circuit diagram showing another embodiment of the energy changing means and the information transmitting means, which radiates light energy, with a block diagram of the information generating means.

FIG. 18 shows another embodiment of the energy changing means 14 and the information transmitting means 15. The transmitting means 15 has a light emitting diode 182. When the information signals generating means 13 generates information through output line 183 and 184, the information signal makes a transistor 185 turn ON, so that a transistor 186 is also placed in a turned ON-state. Consequently, the light emitting diode 182 is made to emit light by the energy given through the input terminals $4T_1$ and $4T_0$. The indicating means 16 which has a photoelectric element, e.g., a photocell or CdS, for receiving the light from the light emitting diode 182. The indicating means 16 receives electric signal through the photoelectric element and indicates the information in the pacemaker by a lamp, a buzzer or the like.

The embodiment of the energy changing means and information transmitting means shown in FIG. 18 is one that is used for the system shown in FIG. 2. It is possible, however, to use the embodiment shown in FIG. 18 for the system shown in FIG. 1, if the input lines 187 and 188 of the information generating means 13 are cancelled. In this case, the information generating means 3 sends the information signal through the lines 137 and 138 by using a little energy of the battery in the pacemaker.

In the case of the embodiment shown in FIG. 18, the light emitting diode 182 is used as a transmitting element. It is possible, however, to use a buzzer, a heater, a vibrator or the like in place of the light emitting diode. In the case of the transmitting energy being sound, it is necessary to employ a sound detecting device, e.g., a microphone, as a detector of the indicating means 6 or 16. In the case of heat, it is necessary to employ a thermoelectric element, e.g., a thermoelectric couple or a thermistor, as the detector of the indicating means 6 or 16. In the case of vibration, it is sufficient to employ a dynamo comprising a magnet core which vibrates according to the vibration and a coil, so that it detects voltage induced across the coil and the indicating means 6 or 16 indicates the information.

It is also possible to append the oscillating circuit shown in FIG. 16 to the circuit shown in FIG. 18.

Figure 19:
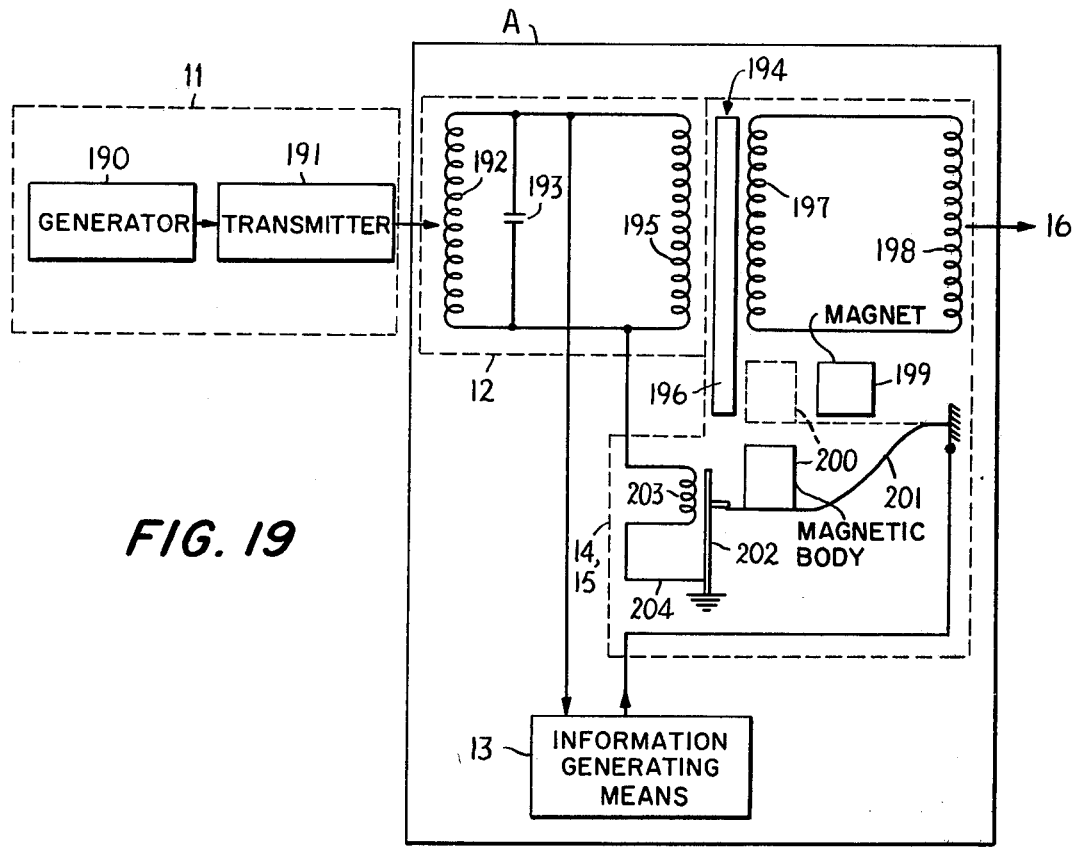
FIG. 19 is a block diagram, which includes a circuit diagram and a schematic representation of a mechanism, showing an embodiment of the system according to the invention.

FIG. 19 shows an embodiment of the energy receiving means 12, energy changing means 14 and the information transmitting means 15. In FIG. 19, the energy supplying means 11 comprises a well-known generator 190 and a transmitter 191 similar to those in the embodiment of FIG. 3, and radiates high-frequency electric wave energy or alternating magnetic field energy.

The energy receiving means 12 has a resonance circuit which comprises a coil 192 receiving the electric wave or alternating magnetic field from the supplying means 11, and a capacitor 193. The inductance of the coil 192 and the capacitance of the capacitor 193 are so determined that the circuit resonates with the electric wave or alternating magnetic field. The high-frequency induced voltage across the coil 192 is supplied to the primary coil 195 of a transformer 194 and the information generating means 13. The transformer 194 which is a part of the information transmitting means 15 has the primary coil 195, a core 196 made of a material having large residual magnetism and a secondary coil 197. High-frequency voltage is induced on the secondary coil 197 from the primary coil 195. An output coil 198 is connected to the secondary coil 197. The output coil 198 changes the induced high-frequency power to electric wave energy, and radiates it to the outside of the pacemaker "A". A magnet 199 is mounted on the base plate at a distance from the core 196. A magnetic material 200 having light weight and large magnetic permeability is provided between the core 196 and the magnet 199 such as shown by a dotted line. The magnetic material 200 is mounted on the end of a spring 201 the other end of which is mounted on the base plate. The magnetic material 200 is usually situated at the place shown by a solid line with the spring 201 deflected. The end of the spring 201 is checked by a clasp 202 mounted on the base plate. The clasp 202 is made of magnetic material having low resistance and is connected with the spring 201 and a line 204 having a coil 203 electrically.

While there appears no information signal from the information generating means 13, the magnetic material 200 is kept at the place shown by the solid line, for the coil 203 is not operated. The high-frequency induced energy on the coil 192 is given to the output coil 198 through the transformer 194 and is radiated to the outside of the pacemaker "A" as electric wave energy. The indicating means 16 receives the electric wave and indicates by sound, light or the like.

When there appears an information signal from the information generating means 13, the coil 203 generates magnetic flux and attracts the clasp 202, so that the spring 201 is off the clasp 202. The magnetic material 200 is carried to the place shown by the dotted line, by the elasticity of the spring 201. Consequently, the flux of the magnet 199 is given to the core 196 of the transformer 194 through the magnetic material 200. The high-frequency energy carried from the transmitter 191 is supplied to the primary coil 195 through the coil 192. However, because of the given flux to the core 196 and the hysteresis of the core 196, there appears an induced e.m.f. having double the primary frequency on the secondary coil 197. The frequency of the secondary induced e.m.f. in case of an information generating from the information generating means 13 is twice that in case of no information generating. The indicating means 16 receive the electric wave having twice the frequency and indicates it by sound, light or the like.

Figure 20:
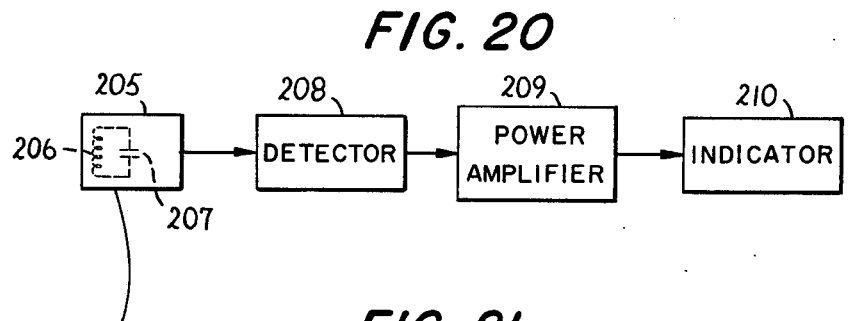
FIG. 20 is a block diagram showing an embodiment of the indicating means which receives electric wave energy or alternating magnetic field energy from the transmitting means.

FIG. 20 shows an embodiment of the indicating means 6 or 16 which receives electric wave energy from the information transmitting means 5 or 15 while the information generating means 3 or 13 generates the information signal. The indicating means 6 or 16 comprises a high-frequency amplifier 205, a detector 208, a power amplifier 209 and an indicator 210. The high-frequency amplifier 205 includes a resonance circuit comprising a receiving coil 206 and a capacitor 207. The constants of the coil 206 and the capacitor 207 are so determined that the circuit resonates with the electric wave radiated from the transmitting means 5 or 15. While the information generating means 3 or 13 generates no information signal, the indicator 210 does not operate, for no electric wave is supplied for the high-frequency amplifier 205. When the information generating means 3 or 13 generates an information signal, the electric wave energy is received by the high-frequency amplifier 205 and the output is detected by the detector 208. The detected output is amplified by the power amplifier 209 and operates the indicator 210, e.g., a lamp or a buzzer.

Figure 21:
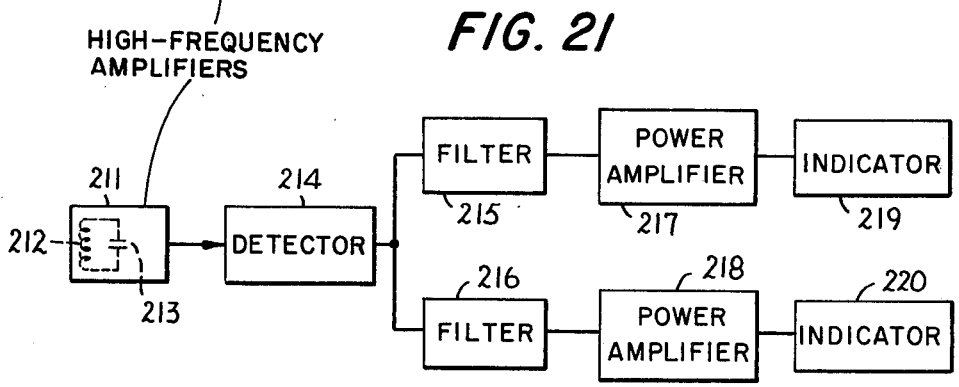
FIG. 21 is a block diagram showing another embodiment of the indicating means which receives modulated electric wave or alternating magnetic field signals.

An embodiment of the indicating means 6 or 16 which receives the electric wave modulated according to the information signal is illustrated in FIG. 21. A high-frequency amplifier 211 includes a resonance circuit comprising a receiving coil 212 and a capacitor 213. The constants of the coil 212 and the capacitor 213 are so determined that the circuit resonates with the modulated carrier wave which is radiated from the information transmitting means 5 or 15. The output of the high-frequency amplifier 211 is detected by a detector 214 and is carried to filters 215 and 216. The filter 215 is a low-frequency band pass filter, which passes the audio frequency wave when there appears no information signal from the information generating means 3 or 13. The filter 216 is a low-frequency band pass filter, which passes the audio frequency wave when there appears an information signal. The output of the filter 215 is amplified by a power amplifier 217 and the output of the filter 216 is amplified by a power amplifier 218. According to the output of the power amplifier 217 or 218, an indicator 219 or 220, e.g., a green or red lamp, is operated. While there appear no information signal from the information generating means 3 or 13, the indicator 219 is operated so that one may understand the means 3 or 13 is generating no information signal. When the information generating means 3 or 13 generates an information signal, the indicator 221 is operated so that one may understand that the information signal is being generated.

Figure 22:
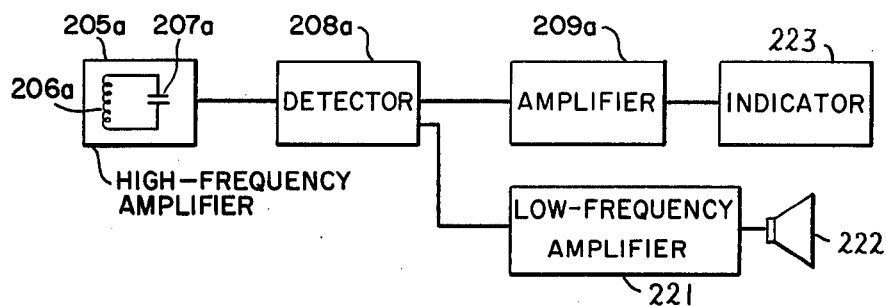
FIG. 22 is a block diagram showing another embodiment of the indicating means which generates beat tones.
Figure 23:
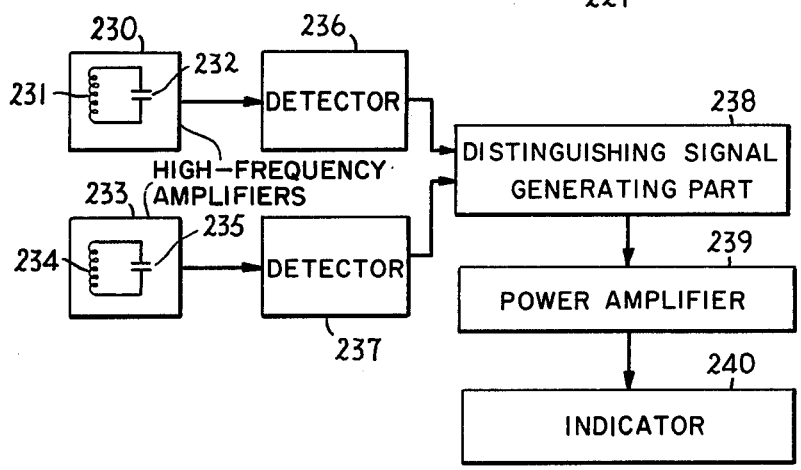
FIG. 23 is a block diagram showing another embodiment of the indicating means which receives electric waves of different frequency.

FIG. 22 shows an embodiment of the indicating means 6 or 16, in the case of using the information transmitting means 5 or 15 including the appended circuit shown in FIG. 16. The indicating means comprises a high-frequency amplifier 205a including a resonance circuit having a receiving coil 206a and a capacitor 207a, and the output of the amplifier 205a is fed to and detected by a detector 208a in a manner similar to that explained hereinabove with reference to FIG. 20. A low-frequency amplifier 221 and a speaker 222 are serially connected to the output terminal of the detector 208a of the indicating means . While there appears no information, the high-frequency amplifier 205a receives only the carrier wave generated by the appended circuit shown in FIG. 16 and the carrier wave is detected by the detector 208a and a corresponding signal is fed through an amplifier 209a to operate the indicator 223. Accordingly, one may check whether the energy receiving means 2 or 12, the energy changing means 4 or 14 and the information transmitting means 5 or 15 operate properly. When there appears an information signal a, beat tone corresponding to the difference of the frequencies of the oscillators in the informaton transmitting means 5 or 15 is generated by the speaker 222, so that it is possible to understand the information. FIG. 23 shows an embodiment of the indicating means 6 or 16 which receives the electric waves having different frequencies from each other, for example, as shown in FIG. 19. The indicating means 6 or 16 comprises high-frequency amplifier 230 and 233, detectors 236 and 237, a distinguishing signal generating part 238, a power amplifier 239 and an indicator 240. The high-frequency amplifier 230 and 233 include a resonance circuit comprising a receiving coil and a capacitor respectively. The constants of the coil 231 and the capacitor 232 in the high-frequency amplifier 230 are so determined that the circuit resonates with the radiated electric wave in the case of generating no information signal from the information generating means 3 or 13. The constants of the coil 234 and the capacitor 235 in the high-frequency amplifier 233 are so determined that the circuit resonates with the radiated electric wave in the case of generating an information signal.

While there appears no information signal, the electric wave having the first frequency radiated from the information transmitting means 5 or 15 is received by the high-frequency amplifier 230 and is carried to the distinguishing signal generating part 238 through the detector 236. The part 238 generates a first distinguishing signal and the signal operates the indicator 240 through the power amplifier 239. The indicator 240 indicates a first expression, e.g., by a buzzer. When there appears an information signal, the electric wave having the second frequency is received by the high-frequency amplifier 233 and is carried to the distinguishing signal generating part 238 through the detector 237. The part 238 generates a second distinguishing signal corresponding to the second frequency. The indicator 240 receives the second signal through the power amplifier 239 and indicates a second expression.

Figure 24:
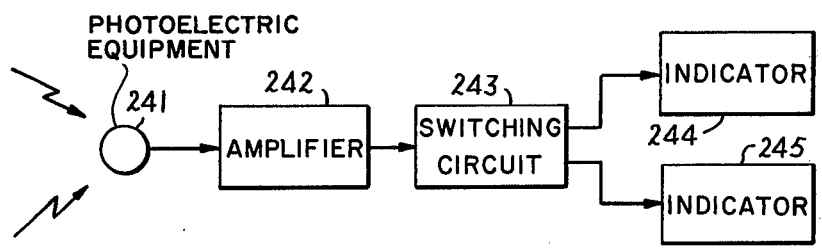
FIG. 24, 25 and 26 are block diagrams showing embodiments of the indicating means, which recieve light energy, sound energy, and mechanical energy respectively.

FIG. 24 shows an embodiment of the indicating means 6 or 16 for receiving light energy from the information transmitting means 5 or 15. The indicating means 6 or 16 comprises a photoelectric element 241, e.g., a photocell or a CdS, an amplifier 242 for amplifying the output of the photo element 241, a switching circuit 243 acting as a switch according to the output level of the amplifier 242, and indicators 254 and 255 operated selectively in connection with the switching operation.

While no light comes in the photoelectric element 241 from the transmitting means 5 or 15, the indicator 244 is operated through the switching circuit 243, so that the indicator indicates, e.g., by a green lamp, that no information signal has been generated in the information generating means 3 or 13.

When an information signal is generated in the information generating means 3 or 13, the photoelectric element receives light energy and the output level of the amplifier 242 goes up. Accordingly, the switching circuit 243 acts to operate the other indicator 245. Consequently, one may understand, e.g., by a red lamp, what information has been generated in the information generating means 3 or 13.

Figure 25:
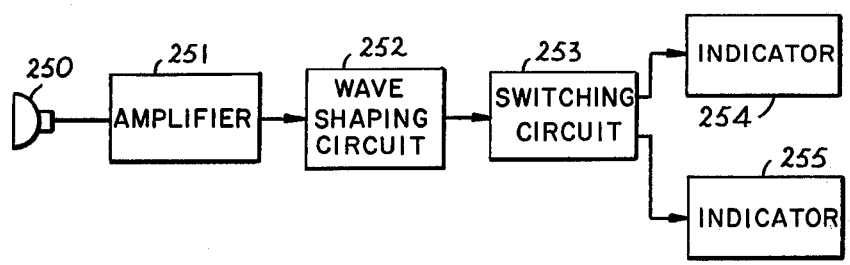

FIG. 25 shows an embodiment of the indicating means 6 or 16 for receiving sound wave energy from the information transmitting means 5 or 15. The indicating means 6 or 16 comprises a microphone 250, an amplifier 251, an wave shaping circuit 252 for generating the output in the case of the output level of the amplifier 251 being higher than predetermined level, a switching circuit 253 acting as a switch according to the output of the wave shaping circuit 252, and indicators 254 and 255 operated selectively in connection with the switching operation.

While no sound wave energy comes in the microphone 250 from the transmitting means 5 or 15, the indicator 254 is selected by the switching circuit 253, so that the indicator indicates that no information signal has been generated. When the sound comes in the microphone 250 from the transmitting means 5 or 15, the output level of the amplifier 251 goes up and the wave shaping circuit 252 generates an output. Accordingly, the switching circuit 253 acts to operate the other indicator 255. Consequently, one may check what the information has been generated in the information generating means 3 or 13.

Figure 26:
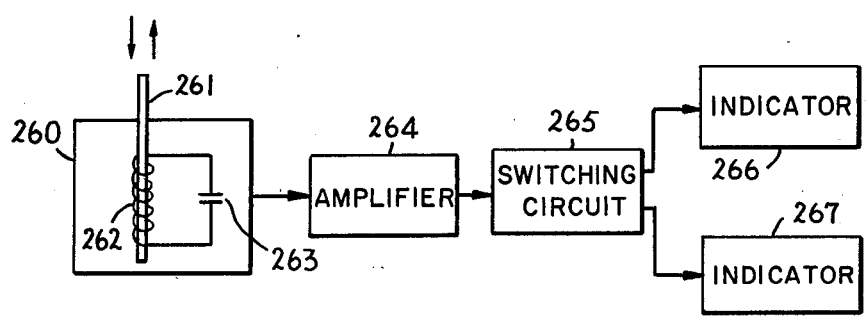

FIG. 26 shows an embodiment of the indicating means 6 or 16 for receiving mechanical energy from the information transmitting means 5 or 15. The indicating means 6 or 16 comprises a pick up part 260, an amplifier 264, a switching circuit 265, and indicators 266 and 267. The pick up part 260 includes a magnet core 261 reciprocating in the direction of arrow heads according to the mechanical vibration of the vibrator in the transmitting means 5 or 15, a coil 262 wounded around the core 261 so that the core 261 may reciprocate in the coil 262, and a capacitor 263 connected to the coil.

While no mechanical energy comes in the pickup part 260 from the transmitting means 5 or 15, the magnet core 261 does not reciprocate, so that the pickup part 260 generates no output. In this case, the switching circuit selects the indicator 266 and makes this operate. Consequently, one may check what no information has been generated in the information generating means 3 or 13.

When the mechanical energy comes in the pickup part 260, the magnet core 261 reciprocates according to the vibration to the vibrator in the transmitting means 5 or 15, so that the coil generates e.m.f. The e.m.f. is supplied for the switching circuit 265 through the amplifier 264. Accordingly, the switching circuit 265 selects the indicator 267 and makes this operate, so that one may check what the information has been generated in the information generating means 3 or 13.

It is possible to provide the indicating means 6 or 16 in the body. In this case, it is possible to make one understand the information in the pacemaker, using mechanical or electric stimulation, heat or the like.

What is claimed is:

1. A system for detecting information about the e.m.f. of series-connected batteries in an artificial cardiac pacemaker comprising: energy supplying means for supplying energy to the artificial cardiac pacemaker from the outside; energy receiving means in the pacemaker for receiving said energy; information generating means for generating an information signal representative of the e.m.f. of the batteries in the pacemaker including a plurality of transistors each of which is connected to one of said batteries such that each transistor changes from one state to the other state when the e.m.f. of the corresponding battery becomes less than a predetermined value; energy changing means receptive of the energy passing through said energy receiving means for changing the energy into an information energy signal according to said information signal; transmitting means for transmitting said information energy signal to the outside of the pacemaker; and indicating means for indicating the information in the pacemaker according to said information energy signal.

2. A system as claimed in claim 1; wherein said information generating means is connected to receive energy passing through said energy receiving means.

3. A system as claimed in claim 1; wherein said energy supplying means includes means for supplying electromagnetic wave energy.

4. A system as claimed in claim 1; wherein said energy supplying means includes means for supplying light energy.

5. A system as claimed in claim 1; wherein said energy supplying means includes means for supplying sound wave energy.

6. A system as claimed in claim 1; wherein said energy supplying means includes means for supplying mechanical energy.

7. A system as claimed in claim 1; wherein said energy receiving means includes means for storing a portion of the received energy.

8. A system as claimed in claim 7; wherein said means for storing a portion of the received energy comprises a capacitor.

9. A system as claimed in claim 7; wherein said means for storing a portion of the received energy comprises a spring.

10. A system as claimed in claim 1; wherein said energy receiving means supplies the received energy to said energy changing means without storing any portion of the received energy.

11. A system as claimed in claim 10; wherein said energy chaning means includes means for converting the frequency of the received energy according to the information signal generated from said information generating means.

12. A system as claimed in claim 1; wherein said energy changing means includes means for modulating the energy passed through said energy receiving means according to the information signal generated from said information generating means.

13. A system as claimed in claim 1; wherein said energy changing means includes means for periodically changing the energy passed through said energy receiving means; and said transmitting means includes means for periodically transmitting the information energy signal.

14. A system as claimed in claim 1; wherein said transmitting means includes means for transmitting electromagnetic wave energy as the information energy signal.

15. A system as claimed in claim 1, wherein said transmitting means includes means for transmitting light energy as the information energy signal.

16. A system as claimed in claim 1; wherein said transmitting means includes means for transmitting sound wave energy as the information energy signal.

17. A system as claimed in claim 1; wherein said transmitting means includes means for transmitting mechanical energy as the information energy signal.

18. A system as claimed in claim 1; wherein said indicating means includes means for providing a sound indication.

19. A system as claimed in claim 1; wherein said indicating means includes means for providing a light indication.

20. A system as claimed in claim 1; wherein said indicating means includes means for providing a stimulation to the human body.

21. A system for detecting information about the e.m.f. of series-connected batteries in an artificial cardiac pacemaker comprising: energy supplying means for supplying electromagnetic wave energy to the artificial cardiac pacemaker from the outside; energy receiving means including a storage capacitor and contained in the pacemaker for receiving said energy; information generating means for generating an information signal representative of the e.m.f. of the batteries in the artificial cardiac pacemaker including a plurality of transistors each of which is connected to one of said batteries such that each transistor changes from one state to the other state when the e.m.f. of the corresponding battery becomes less than a predetermined value; energy changing means for modulating the energy passing through said energy receiving means in accordance with said information signal to accordingly change the energy into an information energy signal; transmitting means for transmitting said information energy signal in the form of an electromagnetic wave to the outside of the pacemaker; and indicating means for providing a sound indicative of the information in the pacemaker according to said information energy signal.

22. A system for detecting information about the e.m.f. of series-connected batteries in an artificial cardiac pacemaker comprising: energy supplying means for supplying electromagnetic wave energy to the artificial cardiac pacemaker from the outside; energy receiving means including a storage capacitor and contained in the pacemaker for receiving said energy; information generating means for generating an information signal representative of the e.m.f. of the batteries in the pacemaker including a plurality of transistors each of which is connected to one of said batteries such that each transistor changes from one state to the other state when the e.m.f. of the corresponding battery becomes less than a predetermined value; energy changing means for modulating the energy passing through said energy receiving means in accordance with said information signal to accordingly change the energy into an information energy signal; transmitting means for transmitting said information energy signal in the form of an electromagnetic wave to the outside of the pacemaker; and indicating means for providing a light indication indicative of the information in the pacemaker according to said information energy signal.

* * * * *